United States Patent [19]

Ulfelder et al.

[11] Patent Number: 4,808,288
[45] Date of Patent: Feb. 28, 1989

[54] ELECTROPHORETIC GEL FOR SEPARATING HEMOGLOBIN VARIANTS

[75] Inventors: Kathi Jo Ulfelder, Santa Ana; William A. Gurske, Placentia, both of Calif.

[73] Assignee: Beckman Instruments, Inc., Fullerton, Calif.

[21] Appl. No.: 798,133

[22] Filed: Nov. 13, 1985

Related U.S. Application Data

[63] Continuation of Ser. No. 588,849, Mar. 12, 1984, abandoned.

[51] Int. Cl.$^4$ .................. B01D 57/02; C07K 3/14; G01N 27/26
[52] U.S. Cl. ................................................... 204/182.8
[58] Field of Search ..................................... 204/182.8

[56] References Cited

U.S. PATENT DOCUMENTS

| | | |
|---|---|---|
| 3,527,712 | 9/1970 | Renn et al. |
| 3,558,459 | 1/1971 | Granstrand et al. |
| 3,873,514 | 3/1975 | Chu et al. |
| 4,139,440 | 2/1979 | Chrambach et al. |
| 4,189,370 | 2/1980 | Boschetti |
| 4,209,373 | 6/1980 | Bluestein et al. |
| 4,292,154 | 9/1981 | Ambler |
| 4,319,976 | 3/1982 | Gurske |

OTHER PUBLICATIONS

The Condensed Chemical Dictionary, 8th Ed, Van Nostrand Reinhold Co., Hawley, p. 832.
Determination of Hemoglobin Variants (Citrate Agar), Corning Medical, Medfield, Mass. 02052.
Titan IV Citrate Hemoglobin Procedure, Helena Laboratories.

*Primary Examiner*—Howard S. Williams
*Attorney, Agent, or Firm*—William H. May; Arnold Grant

[57] ABSTRACT

An electrophoretic gel comprising (a) at least one marine hydrocolloid processed from the class Rodophycea; and (b) a buffer. The electrophoretic gel is characterized in that the buffer (i) is selected from a group consisting of adipic acid, glutaric acid, itaconic acid, maleic acid, malic acid, malonic acid, succinic acid, succinamic acid, and tricarbalyllic acid and (ii) is present in a concentration of about 0.05 to about 0.09 M.

15 Claims, No Drawings

ELECTROPHORETIC GEL FOR SEPARATING HEMOGLOBIN VARIANTS

This is a continuation of co-pending application Ser. No. 588,849, filed on Mar. 12, 1984, now abandoned.

BACKGROUND OF THE INVENTION

1. Field of the Invention

The instant invention pertains to an electrophoretic technique for separating hemoglobin variants and to an electrophoretic gel for use therein.

2. Description of the Prior Art

Electrophoretic techniques for separating hemoglobin variants and electrophoretic gels for use therein are well known to those skilled in the art (1–4). In general, electrophoretic gels employed for separating hemoglobin variants are of the type comprising an agar and a buffer having a pH of from about 6 to about 6.5, the buffer being selected from a group consisting of citrate and ethylenediaminetetraacetic acid (EDTA).

Unfortunately, citrate and EDTA possess several disadvantages. For example, citrate and EDTA exhibit pH drift over time. Therefore, neither citrate nor EDTA can be used in the form of stock solutions capable of storage at room temperature but must either be made fresh or be refrigerated.

Accordingly, it would be very desirable to have a buffer for use in an electrophoretic technique for the separation of hemoglobin variants wherein one or more of the above mentioned problems are either alleviated or removed.

SUMMARY OF THE INVENTION

In accordance with the present invention there is provided an electrophoretic technique for separating hemoglobin variants wherein one or more of the above mentioned problems are either alleviated or removed. The electrophoretic technique of this invention is of the type wherein (a) at least one sample to be assayed is applied to an electrophoretic gel; (b) the electrophoretic gel of step (a) is electophoresed; (c) the electrophoresed gel of step (b) is fixed; and (d) the fixed electrophoretic gel of step (c) is dried. The improved electrophoretic technique of the instant invention is characterized in that a novel electrophoretic gel is employed therein. The novel electrophoretic gel is of the type which comprises (a) at least one marine hydrocolloid processed from the class Rodophycea; and (b) a buffer. The electrophoretic gel is characterized in that the buffer (i) is selected from a group consisting of adipic acid, glutaric acid, itaconic acid, maleic acid, malic acid, malonic acid, succinic acid, succinamic acid, and tricarbalyllic acid and (ii) is present in a concentration of about 0.05 to about 0.09M. The presence of this type of buffer in the electrophoretic gel enables one to alleviate or remove at least one of the above-mentioned problems.

Still other features and attendant advantages of the present invention will become apparent to those skilled in the art from a reading of the following detailed description of the preferred embodiments.

DESCRIPTION OF THE PREFERRED EMBODIMENTS

Preferably, the buffer is present in a concentration of about 0.06 to about 0.08M.

Marine hydrocolloids processed from the class Rodophycea include, but are not limited to, agar, agarose, furcellaran, and carrageenan. Preferably the marine hydrocolloids employed in this invention are selected from a group consisting of agar and mixtures of agar and agarose. The agarose can be either low electroendosmosis agarose, medium electroendosmosis, or high electroendosmosis agarose. More preferably, the agarose is low electroendosmosis agarose.

The electrophoretic gel of the instant invention can optionally further comprise a preservative agent. Typical preservative agents include, but are not limited to, antibiotics, halogenated organic compounds, and inorganic compounds. Readily available preservative agents capable of use herein are sodium azide and ethylmercurithiosalicylic acid, sodium salt.

The electrophoretic gel of the instant invention can also optionally contain an alkylpolyol having 2 to 6 carbon atoms and 2 to 4 hydroxyl groups. Suitable alkylpolyols which can be used herein include, but are not limited to, ethylene glycol, propanediol, butanediol, pentanediol, and glycerol. Preferably, the alkylpolyol has 2 to 4 carbon atoms.

The exact concentrations of the various constituents employed in the electrophoretic gel of the present invention are not critical. However, the electrophoretic gel of the instant invention preferably comprises from about 0.3 to about 1.2 percent low electroendosmosis agarose; from about 0.3 to about 1.2 percent agar; an effective amount of the preservative agent; and a stabilizing amount of the alkylpolyol. More preferably, the electrophoretic gel of the instant invention comprises from about 0.4 to about 1 percent low electroendosmosis agarose; and from about 0.4 to about 1 percent agar. Optimally, the electrophoretic gel of the instant invention comprises about 0.5 percent low electroendosmosis agarose; about 0.5 percent agar; about 0.01 percent ethylmereurithiosalicylic acid, sodium salt; 5 percent 1,2-propanediol and about 0.05M buffer comprising 0.2 percent maleic acid and about 1 percent maleic acid, disodium salt.

The electrophoretic gels of the instant invention can be prepared via any technique well known to those skilled in the art. In general, the gel solution is prepared by mixing the various ingredients present therein while heating the mixture to a temperature of about 80° to about 100° C. The electrophoretic gel can be prepared by either standard molding or casting techniques. The gels can be stored at any convenient temperature, for example from about 2° to about 40° C., preferably from about 18° to about 26° C. It is preferred to store the electrophoretic gels in sealed, plastic trays until ready for use.

Samples can be applied to the electrophoretic gels of the instant invention via any technique used in the prior art, e.g., via a microliter syringe. The electrophoretic gels can be electrophoresed at 50 volts for 30 minutes. If desired, the gels can be fixed in an alcohol:acetic acid mixture such a 60 percent reagent alcohol, 30 percent deionized water, and 10 percent glacial acetic acid. In addition, the gels can optionally be dried at about 80° to about 90° C.

The following examples are provided for the purpose of further illustration only and are not intended to be limitations on the disclosed invention.

EXAMPLES 1-9

Gels comprising 0.5% low electroendosmosis agarose, 0.5% Difco Laboratories Bacto-agar brand agar, 0.1% sodium azide, and 5% 1,2-propanediol were prepared. Each gel also employed a 0.05M concentration of a buffer set forth in Table I.

TABLE I

| Example | Buffers Within Scope of Invention | Prior Art Buffers |
|---|---|---|
| 1 | itaconic acid | |
| 2 | maleic acid | |
| 3 | malic acid | |
| 4 | malonic acid | |
| 5 | succinic acid | |
| 6 | succinamic acid | |
| 7 | tricarbalyllic acid | |
| 8 | | citrate |
| 9 | | EDTA |

The following electrophoretic procedure was employed.

1. Fill each side of an electrophoretic cell with 45 ml of 0.05M buffer.
2. Gently blot surface of gel with a gel blotter. Align template on gel surface. Pipet 5 μl of sample hemolysate having a 2 g/dl hemoglobin concentration onto each sample slot. Wait 5 minutes after last sample is applied, and remove excess sample with template blotter. Discard blotter. Remove and discard template.
3. Place gel onto gel bridge and into electrophoresis cell, matching + and − on bridge with those on the gel. Cover and guide into power supply.
4. Electrophoresis at 50 volts for 35 minutes.
5. Upon completion of electrophoresis, remove gel from the electrophoretic cell and place in gel frame, then in gel holder.
6. Place in fixative solution for 5 minutes.
7. Remove from fixative solution and dry at 70° C. for about 20 minutes.
8. Place dry gel in an 8-amino-7-(3-nitrophenylazo)-2-(phenylazo)-1-naphththol-3,6-disulfonic acid disodium salt blue stain for about 3 minutes.
9. Destain for about 3 minutes.
10. Dry for about 5 minutes.
11. Visually observe patterns.

Succinamic acid and tricarbalyllic acid yielded an Hb A and F separation comparable to that of citrate and itaconic acid, maleic acid, malic acid, malonic acid, and succinic acid yield better Hb A and F separation than obtained with citrate. Furthermore, unlike citrate and EDTA, all of the buffers within the scope of this invention, with the exception of succinic acid, exhibited satisfactory shelf life when stored at room temperature, i.e., exhibited neither bacterial growth nor drift in pH over a period in excess of 4 months.

Based on this disclosure, many other modifications and ramifications will naturally suggest themselves to those skilled in the art. These are intended to be within the scope of this invention.

BIBLIOGRAPHY

1. Gratzer et al., *J. of Chromatography*, 5: 315-329 (1961).
2. Robinson et al., *J. Lab & Clin. Med.*, 50: 645-752 (1957).
3. Barwick et al., *Biochimica et Biophysica Acta*, 668: 485-429 (1981).
4. Schmidt et al., "Basic Laboratory Methods of Hemoglobinophathy Detection", HEW Pub. No. (CDC) 78-8266 (1974).

The embodiments of the invention in which an exclusive property or privilege is claimed are defined as follows:

1. An electrophoretic gel consisting essentially of at least one marine hydrocolloid processed from the class Rodophycea and from about 0.05 to about 0.09M of a buffer selected from the group consisting of adipic acid, glutaric acid, itaconic acid, maleic acid, malic acid, malonic acid, succinic acid, succinamic acid and tricarbalyllic acid.

2. An electrophoretic gel as defined in claim 1 wherein the marine hydrocolloid is selected from the group consisting of agar, agarose, furcellaran and carrageenan.

3. An electrophoretic gel as defined in claim 1 further comprising an effective amount of a preservative agent.

4. An electrophoretic gel as defined in claim 3 wherein the preservative agent is selected from the group consisting of antibiotics and halogenated organic and inorganic compounds.

5. An electrophoretic gel as defined in claim 1 further comprising an alkylpolyol having from 2 to 6 carbon atoms and 2 to 4 hydroxyl groups.

6. An electrophoretic gel consisting essentially of a marine hydrocolloid selected from the group consisting of agar, agarose, furcellaran and carrageenan and from about 0.05 to about 0.09M of a buffer selected from the group consisting of adipic acid, gluratic acid, itaconic acid, maleic acid, malic acid, malonic acid, succinamic acid and tricarbalyllic acid.

7. An electrophoretic gel as defined in in claim 6 wherein the buffer is adipic acid.

8. An electrophoretic gel as defined in claim 6 wherein the buffer is glutanic acid.

9. A electrophoretic gel as defined in claim 6 wherein the buffer is itaconic acid.

10. An electrophoretic gel as defined in claim 6 wherein the buffer is maleic acid.

11. An electrophoretic gel as defined in claim 6 wherein the buffer is malic acid.

12. An electrophoretic gel as defined in claim 6 wherein the buffer is malonic acid.

13. An electrophoretic gel as defined in claim 6 wherein the buffer is succinamic acid.

14. An electrophoretic gel as defined in claim 6 wherein the buffer is tricarbalyllic acid.

15. An electrophoretic gel as defined in claim 6 further comprising an effective amount of a preservative agent and an effective amount of a stabilizing agent.

* * * * *